United States Patent
Perez

(10) Patent No.: US 7,422,599 B2
(45) Date of Patent: Sep. 9, 2008

(54) DEVICE FOR TREATING INFANTS WITH LIGHT

(76) Inventor: Thomas Perez, 3535 W. Irving Park Rd., Chicago, IL (US) 60618

(*) Notice: Subject to any disclaimer, the term of this patent is extended or adjusted under 35 U.S.C. 154(b) by 0 days.

(21) Appl. No.: 11/140,562

(22) Filed: May 27, 2005

(65) Prior Publication Data

US 2005/0288746 A1 Dec. 29, 2005

Related U.S. Application Data

(63) Continuation-in-part of application No. 10/926,209, filed on Aug. 25, 2004, now abandoned.

(60) Provisional application No. 60/503,678, filed on Sep. 17, 2003.

(51) Int. Cl.
*A61N 5/01* (2006.01)

(52) U.S. Cl. .................. 607/93; 607/88; 607/90

(58) Field of Classification Search ........... 128/898; 607/88–94
See application file for complete search history.

(56) References Cited

U.S. PATENT DOCUMENTS

| | | | | |
|---|---|---|---|---|
| 4,907,132 A * | 3/1990 | Parker | | 362/556 |
| 5,021,928 A * | 6/1991 | Daniel | | 362/556 |
| 5,263,925 A | 11/1993 | Gilmore et al. | | |
| 5,474,528 A * | 12/1995 | Meserol | | 604/20 |
| 5,693,049 A | 12/1997 | Mersch | | |
| 5,728,092 A | 3/1998 | Doiron et al. | | |
| 5,934,781 A * | 8/1999 | Whitaker | | 362/26 |
| 6,113,566 A | 9/2000 | Schleicher | | |
| 6,447,537 B1 * | 9/2002 | Hartman | | 607/94 |
| 6,468,433 B1 * | 10/2002 | Tribelski | | 210/748 |
| 6,494,899 B1 * | 12/2002 | Griffin et al. | | 607/88 |
| 6,596,016 B1 * | 7/2003 | Vreman et al. | | 607/88 |
| 6,663,659 B2 * | 12/2003 | McDaniel | | 607/88 |
| 6,811,563 B2 * | 11/2004 | Savage et al. | | 607/88 |
| 6,835,202 B2 * | 12/2004 | Harth et al. | | 607/91 |
| 7,131,990 B2 * | 11/2006 | Bansal et al. | | 607/90 |
| 2002/0074559 A1 | 6/2002 | Dowling et al. | | |
| 2003/0086817 A1 | 5/2003 | Horton | | |
| 2003/0114842 A1 | 6/2003 | Distafano | | |
| 2004/0039428 A1 * | 2/2004 | Williams et al. | | 607/91 |
| 2005/0177208 A1 * | 8/2005 | Irwin | | 607/94 |

\* cited by examiner

*Primary Examiner*—Henry M Johnson, III
(74) *Attorney, Agent, or Firm*—Adam K. Sacharoff; Much Shelist

(57) ABSTRACT

A device for providing light, preferably UV light to infants and/or children. The device comprises a housing, inside the housing are one or more light sources adapted to emit light at a therapeutic wavelength or wavelengths. A series of apertures in the housing are adapted to align a plurality of light guides with the light source(s). The light guides conduct light to the patient. The light guides are preferably attached to a light guide holding element. The holding element is preferably a panel which is adjustably placed above the patient. The light guides can either provide light directly to the patient or the panel can be the light providing surface.

10 Claims, 2 Drawing Sheets

DEVICE FOR TREATING INFANTS WITH LIGHT

This application is a continuation-in-part of U.S. application Ser. No. 10/926,209 filed Aug. 25, 2004, now abandoned that claims the benefit of U.S. Provisional Application No. 60/503,678 filed Sep. 17, 2003.

BACKGROUND OF THE INVENTION

1. Field of the Invention

The present invention relates to a device for treating infants with light at one or more therapeutic wavelengths.

2. Background of the Prior Art

Ultraviolet (UV) light can be used to treat a multitude of medical problems, including for example bacterial, viral and fungal infections, poisoning, fatigue, Alzheimer's disease, allergies and asthma, rheumatic diseases and arthritis, diabetes, hepatitis, and cancer. UV light sterilizes the blood and acts as an antibiotic.

The UV light is applied either to the patient's skin or directly to the blood. If the UV light is applied to the skin it is typically provided to the patient's skin either with a wrap or lamp.

UV light is commonly used to treat jaundiced babies. Because infant's skin is thin and the blood vessels are close to the surface, UV light is typical applied to the skin when treating jaundiced babies.

Applying the UV light directly to a patient's blood supply is known as photoluminescence or UV blood illumination (UBI). UV blood illumination increases oxygen, destroys toxins and boosts the immune system.

In prior art UBI, a small amount of blood is drawn from the patient, up to about 250 cc. The body has about 5.6 L of blood. The blood that is drawn travels through a cuvette or glass chamber. The blood is repeatedly illuminated with UV light and then returned to the body. The process is repeated, typically a day or several days later. These treatments are time consuming, and require regular trips to a medical facility. In addition, trained personal must be available to provide the treatments.

There is a need for a method of providing UV light to a patient's entire blood supply, not just a small portion of it. There is a need for a system that is convenient for the patient, which does not require regular doctor visits. There is a need for a simple system that can be used by the patient in his home.

There is a need for a system that allows for round the clock treatments or other regular treatments such as pulsed treatment or automatic periodic treatments.

There is a need for a blood illuminator that reduces the risk of infection from removing blood. There is a need for a system that reduces the number of needle sticks a patient must endure.

There is a need for a system that allows the blood to be treated on an as needed basis, such as based on how the patient is feeling at a particular time.

SUMMARY OF THE INVENTION

The Invention is a device for providing light, preferably UV light to infants and/or children with hepatitis. The device comprises a housing, inside the housing are one or more light sources adapted to emit light at a therapeutic wavelength or wavelengths. The device has an on/off switch. A series of apertures in the housing are adapted to connect a plurality of light guides with the light source(s). The light guides conduct light to the baby or patient. The light guides are preferably attached to a light guide holding element. The holding element is preferably a panel which is slidably held in place above the patient. The light guides can either provide light directly to the patient or the panel can be the light providing surface. The panel may be a light guide to evenly spread the light along a bottom surface or it may have a diffuse panel to reduce the amount of light on the skin.

DETAILED DESCRIPTION OF THE INVENTION

Figure 1:
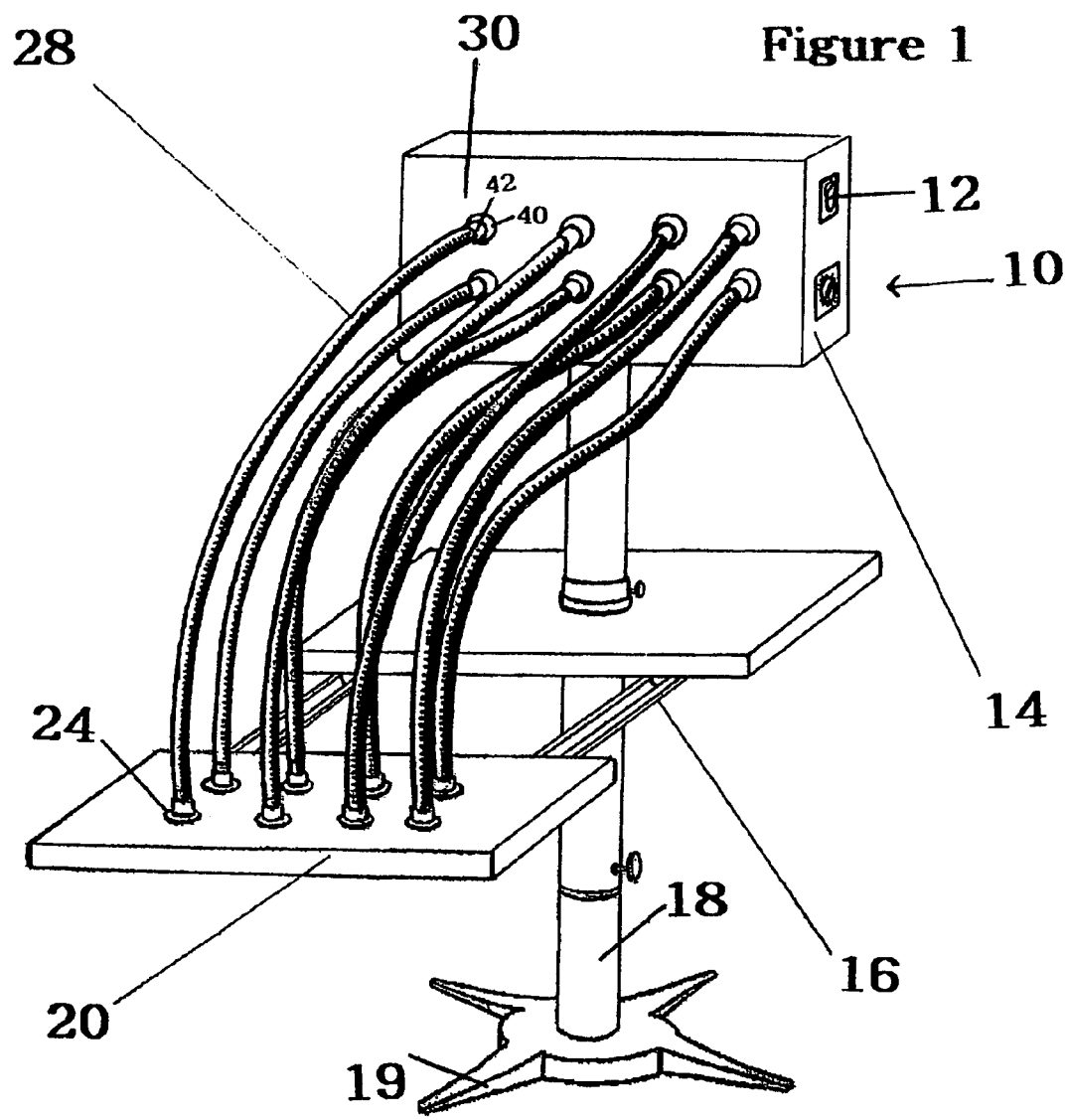
FIG. 1 is treatment lamp.
Figure 2:
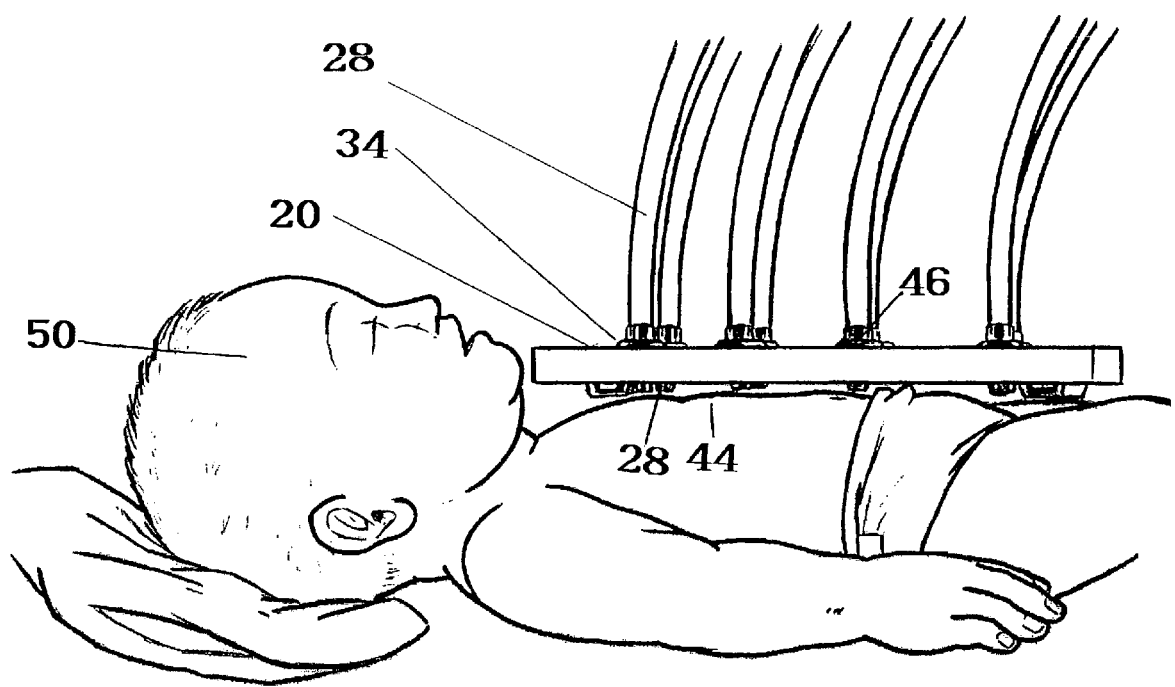
FIG. 2 is a patient being treated with the treatment lamp.

Light at a therapeutic wavelength or wavelengths is used to treat many diseases including infections, poisoning, fatigue, allergies, hepatitis, cancer and HIV. UV light increases the oxygen combining power of the blood, destroys toxins, viruses, fungi, bacteria, and boosts the immune system. UV light also sterilizes the blood and acts as an antibiotic. Preferably, UV light at a therapeutic wavelength(s) is used. More preferably the light is either UV-A or UV-C light is utilized in the present invention. For some conditions and/or diseases UV-A light is more effective than UV-C and for other conditions and/or diseases UV-C light is more effective than UV-A light. The wavelengths or wavelengths of light to be used to treat the patient are selected based on the wavelength or wavelength that will best treat the condition or disease of the patient. For example, UV-C light is preferred for treating hepatitis while UV-A is more effective for cancer.

The invention is a device 10 for providing light at a therapeutic wavelength to Infants and/or children 50 with hepatitis or other conditions or diseases. Preferably, the therapeutic wavelength is one or more UV wavelengths. More preferably, the therapeutic wavelengths is UV-A light, UV-C light or a combination thereof.

The treatment device 10 comprises a housing 30, inside the housing are one or more light sources adapted to emit light at a therapeutic wavelength or wavelengths. The device has an manual on/off switch 12 and an emergency disconnect.

A series of apertures 40 in the housing 30 are adapted to align a plurality of light guides 28 with the light source(s). The light guides 28 pass through a rubber gasket 42 at the aperture 40 and align with a light source such as a medical grade UV bulb or LED. The light guides 28 conduct light to the baby or patient 50. Light guides 28 are preferably attached to a light guide holding element 20. Holding element 20 is preferably a panel 26 which is slidably held in place above the patient 50. The light guides 28 can either provide light directly to the patient 50 or the panel 26 can be the light providing surface. In one embodiment, a series of apertures 44 in the light guide holding element 20 align the light guides 28 over the patient 50. Preferably, the light guides 28 are arranged in a symmetrical manner to evenly spread the light over the patient 50. The light guides may pass through rubber gaskets 46 in the holding element 20. The rubber gaskets 44 adapted to maintain the alignment of the light guides. 28 Alternatively, light guides 28 may be aligned in a pattern or asymmetrical shape. For example, the light guides 28 may be arranged focus more of the light in a particular area of the patient's body 50 such as the core. In another alternative, the panel 26 may be a light guide to evenly spread the light along a bottom surface or it may have a diffuse bottom surface to reduce the amount of light on the patient's 50 skin.

Holding element 20 is used to ensure uniform radiation of the patient 50 without providing too much light which may burn or damage the skin. The light is filtered through the light guides 28 so that its power is diluted by the time it irradiates the patient 50. There is a balance between providing light strong enough to improve the condition, disease or symptoms of the patient and weak enough so as to not burn or harm the patient.

The light source(s) emit radiation at one or more therapeutic wavelength. The light sources may be medical grade UV light, LED or other light sources. The light sources preferably emit UV-C or UV-A light or combinations thereof.

The housing 30 is preferably mounted on a hospital pole 18. The pole may be a stationary pole or optionally have wheels on its base 19 allowing it to be moved easily. Holding element 20 is adjustable mounted to the pole 18. Preferably, holding element 20 is adjustable in at least two directions, up and down to adjust the distance of the holding element 20 above the patient 50 and forward and backward so that holding element 20 is be aligned directly over the patient 50. Holding element 201 may also be adjustable left and right by pivoting or swiveling it.

Patient 50 can be treated by aligning the holding element 20 over the patient and turning on the light source whenever a treatment is needed. Alternatively, the panel can remain over the patient's bed and be turned on and off manually or a controller could automatically turn off the light source after a set treatment time, such as 20 minutes. The controller, such as a computer or other smart interface, can be adapted to limit the number of treatments given time period, limits the total amount of treatment time in a given time period, automatically provides treatments, pulse the light source, or provides only particular wavelengths. The computer or other smart interface could keep a treatment record. The computer or other smart interface could communicate wirelessly, via the Internet or through other electronic means to automatically update the doctor's treatment records. Computer preferably can automatically adjust treatment time, wavelength or other factors based on patient input, doctor orders or other data.

I claim:

1. A therapeutic light treatment device comprising:
   a housing having at least a bottom and a first side wall, the first side wall having a plurality of apertures;
   a light source contained within the housing, said light source emitting UV-C light;
   a first panel positioned at a distance from the housing and having a plurality of apertures;
   a plurality of light guides separately having first ends in communication with the plurality of apertures in the first side wall and separately having second ends in communication with the plurality of apertures in the first panel, wherein the plurality of light guides provide a medium to direct the UV-C light from the light source contained within the housing out the apertures in the first panel;
   a portable stand secured to the bottom of the housing and extending downwardly such that the treatment device may be supported on a surface and moved to a desired location;
   a second panel secured to the stand at a position below the housing;
   a sliding horizontal guide secured to the first panel and slidably attached to the second panel, such that the first panel may be horizontally adjusted from one position to another position with respect to the second panel and stand; and
   a plurality of gaskets positioned in the apertures in the first panel and positioned in the plurality of apertures in the side of the housing wherein a portion of each first and second ends of the plurality of light guides may be secured to the housing and first panel, respectively, when in communication with the gaskets.

2. The therapeutic light treatment device of claim 1, wherein the stand is vertically adjustable.

3. The therapeutic light treatment device of claim 1, wherein the light guides have a liquid core.

4. The therapeutic light treatment device of claim 1 further comprising a controller system, the controller system automatically controls the light source.

5. The therapeutic light treatment device of claim 4, wherein the controller system automatically controls the light source by pulsing the light, by automatically shutting off the light after a specified period of time, by automatically activating the light source at a specified time or by combinations thereof.

6. A therapeutic light treatment device comprising:
   a housing having at least a bottom and a first side wall, the first side wall having a plurality of apertures;
   a light source contained within the housing, said light source emitting UV-C light;
   a panel positioned at a distance from the housing and having a top side with a plurality of apertures and having a bottom surface with a plurality of openings;
   a plurality of light guides separately having first ends in communication with the plurality of apertures in the first side wall and separately having second ends in communication with the plurality of apertures in the top side of the panel, wherein the plurality of light guides provide a medium to direct the UV-C light from the light source contained within the housing out the plurality of openings in the bottom surface of the panel;
   a stand secured to the bottom of the housing, such that the treatment device may be supported on a surface;
   a sliding horizontal guide secured to the panel and extending from the stand, such that the panel may be horizontally adjusted from the stand; and
   a diffuser positioned about the bottom surface of the panel to reduce the amount of UV-C light existing the panel.

7. The therapeutic light treatment device of claim 6, wherein the light guides have a liquid core.

8. The therapeutic light treatment device of claim of 7, wherein the plurality of apertures in the panel and the plurality of apertures in the side of the housing contain gaskets around the ends of the light guides.

9. The therapeutic light treatment device of claim 6 further comprising a controller system, the controller system automatically controls the light source.

10. The therapeutic light treatment device of claim 9, wherein the controller system automatically controls the light source by pulsing the light, by automatically shutting off the light after a specified period of time, by automatically activating the light source at a specified time or by combinations thereof.

* * * * *